US006086546A

United States Patent [19]

Morris et al.

[11] Patent Number: 6,086,546

[45] Date of Patent: Jul. 11, 2000

[54] GYNECOLOGICAL SAMPLERS

[75] Inventors: Edward Patrick Morris, 2 Arnqask Road, Catford, SE6 1XU London; Paul Benjamin Ridout, Hythe, both of United Kingdom

[73] Assignees: Edward Patrick Morris; Smiths Industries Public Limited Company, both of London, United Kingdom

[21] Appl. No.: 09/266,592

[22] Filed: Mar. 11, 1999

[30] Foreign Application Priority Data

Apr. 1, 1998 [GB] United Kingdom .................. 9807075

[51] Int. Cl.[7] .................. A61B 10/00

[52] U.S. Cl. .................. 600/571; 600/562; 604/55

[58] Field of Search .................. 600/562, 569, 600/570, 571, 573; 604/22, 54, 55, 280

[56] References Cited

U.S. PATENT DOCUMENTS

| | | | |
|---|---|---|---|
| 3,088,454 | 5/1963 | Shute | 600/571 |
| 3,438,366 | 4/1969 | Kariher et al. | 600/570 |
| 3,540,432 | 11/1970 | Ayre | 600/571 |
| 3,766,907 | 10/1973 | Muenzer | 600/573 |
| 4,311,140 | 1/1982 | Bridgman | 128/276 |
| 4,534,362 | 8/1985 | Schumacher et al. | 600/562 |
| 4,620,548 | 11/1986 | Hasselbrack | 600/571 |
| 5,069,224 | 12/1991 | Zinnanti, Jr. | 600/565 |
| 5,083,572 | 1/1992 | Pokorny | 600/573 |
| 5,464,022 | 11/1995 | Mohajer | 128/758 |
| 5,807,282 | 9/1998 | Fowler | 600/571 |

FOREIGN PATENT DOCUMENTS

| | | | |
|---|---|---|---|
| 2602-414 | 2/1988 | France | 600/570 |
| 3539444 | 5/1987 | Germany . | |
| 892548 | 3/1962 | United Kingdom . | |
| 1158159 | 7/1969 | United Kingdom . | |
| WO 9724071 | 7/1997 | WIPO . | |

*Primary Examiner*—Cary O'Connor
*Assistant Examiner*—Charles Marmor, II
*Attorney, Agent, or Firm*—Pollack, Vande Sande & Amernick

[57] ABSTRACT

An endometrial sampler has an outer catheter and an inner plunger slidable within the catheter. The catheter has a coaxial opening at its tip and two side openings located diametrically opposite one another close to the tip, the side openings being elongate along the axis of the catheter. The tip of the plunger projects into the tip opening to form a smooth surface to the sampler. An O-ring seal on the plunger is located rearwardly of the side openings so that suction is applied to both the side openings and the tip opening when the plunger is pulled rearwardly.

9 Claims, 2 Drawing Sheets

GYNECOLOGICAL SAMPLERS

BACKGROUND OF THE INVENTION

This invention relates to gynecological samplers.

Gynecological samplers are used to take samples from the uterus, cervix or the like, such as endometrial cells lining the uterus. The sampler usually comprises a plastic catheter and a plunger device movable within the catheter. The tip of the catheter is closed and cells are admitted via a single, circular side opening close to the tip when suction is applied by pulling back on the plunger. The problem with such samplers is that it can be difficult to obtain large numbers of cells. Examples of gynecological samplers are described in, for example: FR 2602414, WO 97/19642, U.S. Pat. No. 4,534,362, GB 2126100, U.S. Pat. No. 5,069,225, U.S. Pat. No. 5,807,282, U.S. Pat. No. 5,464,022, U.S. Pat. No. 4,877,037, U.S. Pat. No. 4,662,381, U.S. Pat. No. 4,396,022, U.S. Pat. No. 4,340,066 and "The Pipelle: A disposable device for endometrial biopsy" by E Cornier, Am. J. Obstet. Gynecol. Jan. 1, 1984, pp109–110.

SUMMARY OF THE INVENTION

It is an object of the present invention to provide an improved gynecological sampler.

According to the present invention there is provided a gynecological sampler having an outer catheter and an inner plunger, the outer catheter having a cylindrical wall with at least one side opening towards its patient end, the catheter having at least one further opening towards its patient end, and the plunger being slidable from a first forward position to a second rear position so that suction is applied to draw material into the catheter through the openings.

Preferably, the catheter has two side openings in the cylindrical wall of the catheter, such as located diametrically opposite one another, and the side openings are preferably elongate along the axis of the catheter. Preferably, the catheter also has an opening at its tip located coaxially of the catheter. The plunger preferably projects into the opening at the tip of the catheter so as to form a smooth tip to the sampler. The plunger may have an O-ring seal, the O-ring seal being located to the rear of each side opening when the plunger is fully inserted in the catheter.

An endometrial sampler according to the present invention, will now be described, by way of example, with reference to the accompanying drawings.

DETAILED DESCRIPTION OF THE PREFERRED EMBODIMENT

Figure 1:
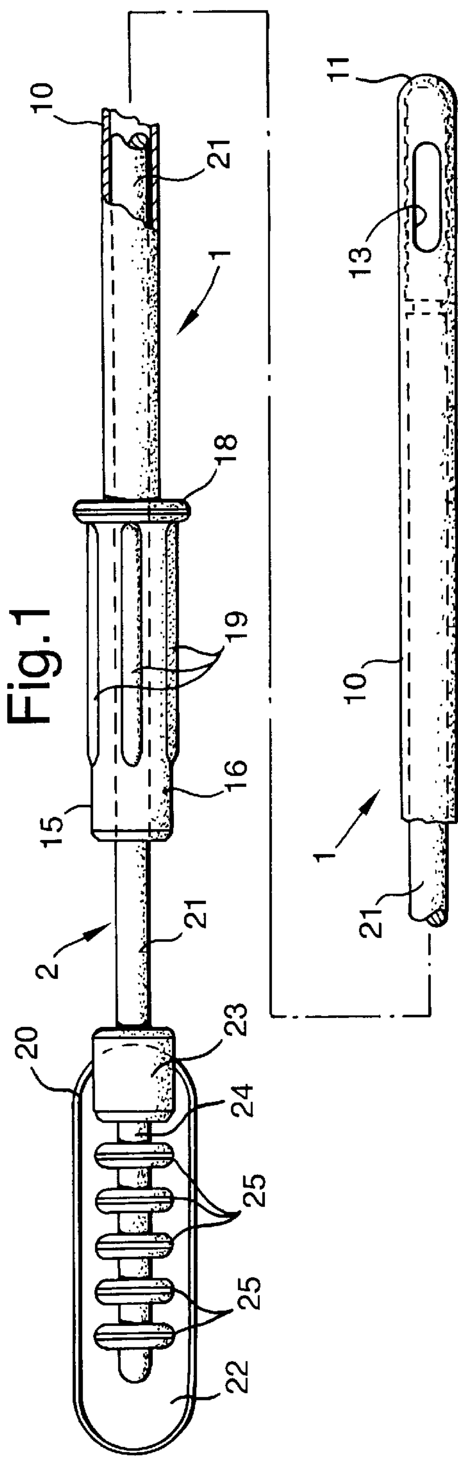
FIG. 1 is a plan view of the sampler.
Figure 2:
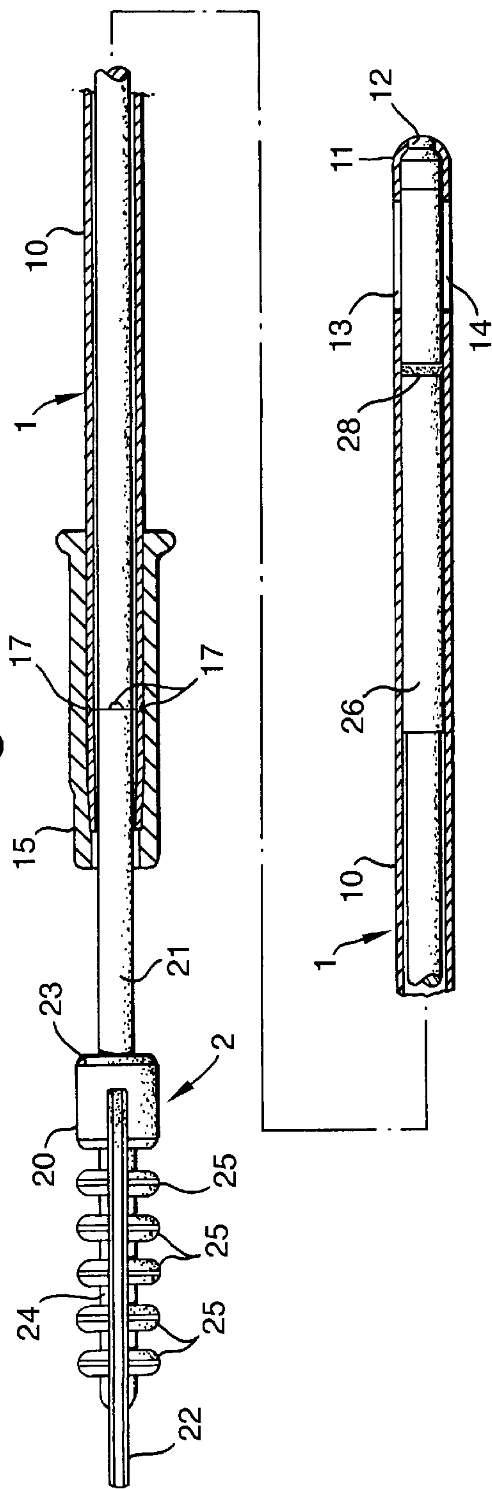
FIG. 2 is a cross-sectional side elevation view of the sampler.
Figures 3, 4:
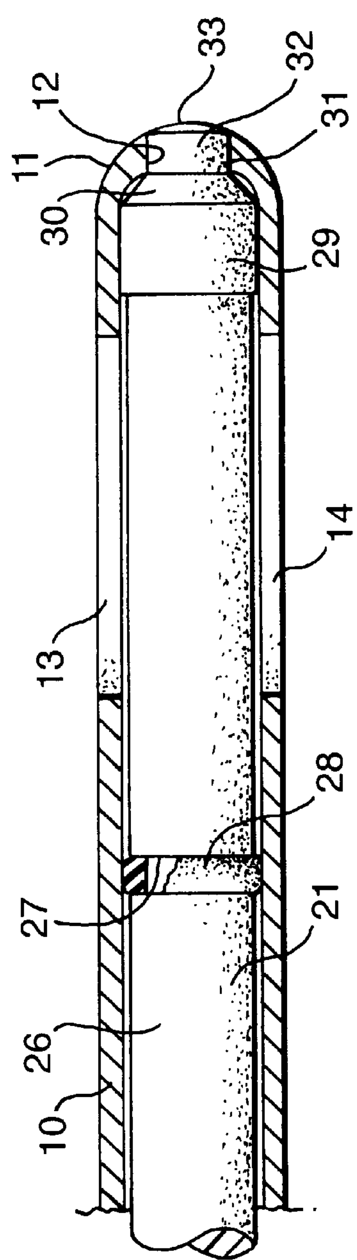
FIG. 3 is a cross-sectional side elevation view of the tip of the sampler to an enlarged scale.
FIG. 4 is a side elevation view of the tip of the plunger to an enlarged scale.

The sampler comprises an outer catheter 1 and a plunger 2 that is slidable axially within the catheter.

The catheter 1 is typically about 250 mm long and has tubular shaft 10 of cylindrical shape with an outer diameter of about 3 mm and an inner diameter of about 2.4 mm. The shaft 10 is extruded from a flexible plastics material such as polypropylene and is end formed at its forward, patient end 11 to give it a rounded tip with a coaxial opening 12 of circular shape having a diameter about half the external diameter of the shaft. The shaft 10 is also formed with two further openings close to the forward, patient end tip in the form of side openings 13 and 14. The side openings 13 and 14 are located diametrically opposite one another set back rearwardly from the tip 11 by a distance of about 4 mm in a cylindrical region of the shaft 10. Each opening 13 and 14 is elongated axially, being about 2 mm wide and 4 mm long with rounded ends. The catheter 1 also includes a collar 15 at its rear or machine end 16 into which the rear end of the shaft 10 is fixed. The collar 15 has five internal pips 17 about half way along its length, which help constrict and grip the outside of the shaft 10. The collar 15 has an external annular rib 18 at its forward end and several longitudinal ribs 19, which help provide a secure grip when held between the finger and thumb. A small clearance between the outside of the plunger 2 and the rear end of the shaft 10 allows for trapped air to be expelled from the catheter as the plunger is pulled rearwardly. The shaft 10 of the catheter is preferably marked with distance markings (not shown) from its tip.

The plunger 2 also acts as a stylet to stiffen the catheter 1 during insertion. The plunger 2 is longer than the catheter 1, being typically about 313 mm long and comprises a rear handle 20 and a rod 21 extending forwardly from the handle. The plunger is made from a relatively stiff but bendable material such as polypropylene or nylon. The handle 20 is about 23 mm long and comprises a flat plate 22 with a cylindrical boss 23 at its forward end. The handle has gripping projections on its upper and lower surface provided by an axial spine 24 and five lateral ribs 25 on each surface. The rod 21 is solid, 290 mm long and of circular section with a diameter of 2 mm along most of its length. The diameter of the rod 21 is increased slightly to 2.2 mm along a region 26 extending forwardly from a location 32 mm from the tip of the rod. An annular groove 27, with a curved profile, is formed around the rod 21 in the region 26 at a location about 12.5 mm from the tip. The groove 27 serves to retain an O-ring seal 28. The diameter of the rod 21 is further increased to 2.35 mm along a region 29, which is about 1.5 mm long. This enlarged region 29 adjoins a short tapered region 30, about 0.5 mm long. The tapered region 30 adjoins a nose portion 31 comprising a rear cylindrical portion 32 and a forward domed portion 33, the diameter of the rear portion being 1.4 mm.

When the plunger 2 is located in the catheter 1 in its fully forward position, the nose portion 31 projects into the tip opening 12 of the catheter as a close fit and with the domed portion 33 of the rod 21 forming a smooth continuation of the rounded tip 11 of the catheter and closing the opening. Because the plunger 2 extends to the tip of the catheter 1, it acts to stiffen it along its entire length and, in particular, it stiffens it in the region of the openings 12, 13 and 14. The enlarged portion 29 of the rod 21 is a close sliding fit within the catheter 1 and is located forwardly of the side openings 13 and 14. The region 26, being slightly smaller in diameter, allows a small clearance between its outside and the inside of the catheter 1 but the O-ring seal 28 provides an effective, fluid-tight sliding seal with the inside of the catheter at a location to the rear of the side openings 13 and 14 thereby closing the side openings.

The sampler is used by inserting its forward end 11 into the uterus with the plunger 2 pushed fully forwardly in the catheter 1. The next step is for the user to withdraw the plunger 2, while leaving the tip 11 of the catheter 1 in substantially the same position. As the plunger 2 is withdrawn, it opens the openings 12, 13 and 14 and applies a suction force to them. The plunger 2 is withdrawn to its fall extent, as limited by engagement of the enlarged portion 26 with the constriction in the catheter 1 caused by the pips 17 in the collar 15. Engagement with the surrounding tissue limits the rate at which fluid and cells in the vicinity are sucked into the catheter 1. The patient tip 11 of the sampler is then rotated and rubbed gently backwards and forwards a few times against the endometrium lining the uterus to free endometrial cells. It has been found that the elongated shape of the side openings 13 and 14 significantly increases the effectiveness in loosening of these cells because the longer perimeter of each opening compared with a conventional circular opening causes an abrasive action over a wider area. Also, the use of two openings 13 and 14 on opposite sides further enhances the liberation of cells. The rounded tip 11 of the sampler will also cause detachment of some cells. The suction force applied by withdrawing the plunger 2 sucks the loosened cells into the catheter during this rubbing action.

The construction of the sampler has several advantages. In addition to providing an increased liberation of cells, the different orientation of the three openings helps ensure collection of cells from all around the tip of the sampler, leading to an increased number of collected cells. Another advantage is that the large area side openings enable the sample to be expelled more easily than in previous samplers where it was often necessary to cut off the tip of the sampler before expelling the sample. Also, the elongated shape of the side openings gives them a greater cross-section and helps reduce damage to the cells that might otherwise be caused by passage into and out of the sampler through a constricted opening.

What we claim is:

1. A gynecological sampler comprising: an outer catheter, said outer catheter having a forward end and a rear end, a cylindrical wall, at least one side opening in said cylindrical wall towards said forward end, and an end opening located coaxially of said catheter and forwardly of said side opening; and a plunger with a forward end and a rear end, said plunger being slidable from a first forward position to a second rear position so that suction is applied to draw material into said catheter through said openings.

2. A sampler according to claim 1, further including is a second side opening in said cylindrical wall.

3. A sampler according to claim 2, wherein said two side openings are located diametrically opposite one another.

4. A sampler according to claim 1, wherein said side opening is elongate along an axis of said catheter.

5. A sampler according to claim 1, wherein said plunger projects into said coaxial opening forming a smooth tip to the sampler.

6. A sampler according to claim 1, wherein said plunger has an O-ring seal, and wherein said O-ring seal is located to the rear of said side opening when said plunger is in said first position.

7. An endometrial sampler comprising: an outer catheter, said outer catheter having a forward end, a rear end, a cylindrical wall, and two elongate side openings in said cylindrical wall towards said forward end; and a plunger with a forward end and a rear end, said plunger being slidable from a first forward position where the forward end of said plunger is located forwardly of said openings, to a second rear position so that suction is applied to draw endometrial material into said catheter through said openings.

8. An endometrial sampler according to claim 7, wherein said catheter includes a third opening located coaxially at said forward end of said catheter, and wherein said plunger extends into said third opening when said plunger is in its first position.

9. An endometrial sampler comprising: an outer catheter, said outer catheter having a forward end, a rear end, a cylindrical wall, two side openings in said cylindrical wall towards said forward end, and a third coaxial opening at the tip of the catheter; and a plunger with a forward end extending beyond said side openings, a rear end, and a seal located between said forward and rear ends of said plunger, wherein said plunger is slidable from a first position in which said forward end closes said third opening and said seal seals with said catheter to the rear of said two side openings to a second position in which said forward end of said plunger is located rearwardly of all three openings and endometrial material is drawn into said catheter through said openings.

* * * * *